(12) United States Patent
Yang et al.

(10) Patent No.: US 9,777,313 B2
(45) Date of Patent: Oct. 3, 2017

(54) SILVER NANOCLUSTER PROBE AND TARGET POLYNUCLEOTIDE DETECTION METHOD USING SAME, AND SILVER NANOCLUSTER PROBE DESIGN METHOD

(75) Inventors: Seong Wook Yang, Seoul (KR); Tom Vosch, Heusden-Zolder (BE)

(73) Assignee: SEOULIN BIOSCIENCE CO., LTD., Bundang-Gu Seongnam-Si Gyeonggi-Do (KR)

( * ) Notice: Subject to any disclaimer, the term of this patent is extended or adjusted under 35 U.S.C. 154(b) by 76 days.

(21) Appl. No.: 14/423,088

(22) PCT Filed: Aug. 22, 2012

(86) PCT No.: PCT/KR2012/006659
§ 371 (c)(1),
(2), (4) Date: Feb. 20, 2015

(87) PCT Pub. No.: WO2014/030778
PCT Pub. Date: Feb. 27, 2014

(65) Prior Publication Data
US 2015/0225781 A1    Aug. 13, 2015

(30) Foreign Application Priority Data
Aug. 22, 2012    (KR) .................. 10-2012-0091554

(51) Int. Cl.
*C12Q 1/68* (2006.01)
*C07H 21/00* (2006.01)
(52) U.S. Cl.
CPC ......... *C12Q 1/6816* (2013.01); *C12Q 1/6876* (2013.01)
(58) Field of Classification Search
CPC .................................. C12Q 1/68; C07H 21/00
See application file for complete search history.

(56) References Cited

U.S. PATENT DOCUMENTS

| 2005/0144669 | A1 * | 6/2005 | Reinhart | ............ | C12N 15/8218 800/285 |
| 2010/0105024 | A1 | 4/2010 | Xu et al. | | |
| 2011/0212540 | A1 * | 9/2011 | Yeh | ...................... | C12Q 1/6816 436/501 |

FOREIGN PATENT DOCUMENTS

| KR | 1020090060635 A | 6/2009 | | |
| KR | 10-0981987 | 9/2010 | | |
| KR | 1020110103009 A | 9/2011 | | |
| KR | 10-1133242 | 4/2012 | | |
| WO | WO 2006/034368 | * | 3/2006 | ............... A01H 1/00 |

OTHER PUBLICATIONS

Diez et al., Minireview : Fluorescent silver nanoclusters Nanoscale 3:1963 (2011).*
Guo et al., Highly Sequence-Dependent Formation of Fluorescent Silver Nanoclusters in Hybridized DNA Duplexes for Single Nucleotide Mutation Identification JACS 132 : 932 (2010).*
Nolan et al., A Simple Quenching Method for Fluorescence Background Reduction and Its Application to the Direct, Quantitative Detection of Specific mRNA. Analytical Chemistry 75(22) : 6236 (2003).*
Shah et al.,Design Aspects of Bright Red £missive Silver Nanoclusters/DNA Probes for MicroRNA Detection. ACSNano 6(10) : 8803 (2012).*
Yeh et al., A DNA-Silver Nanocluster Probe That Fluoresces upon Hybridization. Nano Letters 10 :3106 (2010).*
Lin et al., "Attomolar Ultrasensitive MicroRNA Detection by DNA-Scaffolded Silver-Nanocluster Probe Based on Isothermal Amplification," *Anal. Chem.*, 5 pages.
Richards et al., "Oligonucleotide-Stabilized Ag Nanocluster Fluorophores," *J. Am. Chem. Soc.*, 2008, 130, 5038-5039.
Yang et al., "Rapid Detection of MicroRNA by a Silver Nanocluster DNA Probe," *Anal. Chem.*, 2011, No. 83, 6935-6939, S1-S6.
PCT, "International Search Report," PCT/KR2012/006659, Mar. 15, 2013, 4 pages.

\* cited by examiner

*Primary Examiner* — Ethan C Whisenant
(74) *Attorney, Agent, or Firm* — Haynes and Boone, LLP

(57) ABSTRACT

The present invention provides a silver nanocluster probe which comprises a silver nanoparticle binding region and a specific nucleotide sequence region that specifically binds to a target polynucleotide, wherein the silver nanocluster probe is configured such that it will emit detectable light when silver nanoparticles bind to the silver nanoparticle binding region to form a silver nanocluster, but light emission from the silver nanocluster probe will decrease or decay when the target polynucleotide binds to the specific nucleotide sequence region. According to the present invention, either the presence of a target polynucleotide in a sample or a mutation in the target polynucleotide can be detected in a rapid and convenient manner by determining whether light emission decreases or decays when the target polynucleotide binds to the specific nucleotide sequence region of the silver nanocluster probe that emits detectable light.

20 Claims, 8 Drawing Sheets

FIG. 2
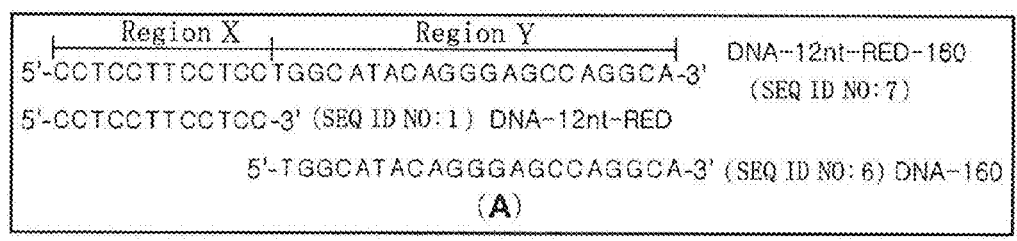
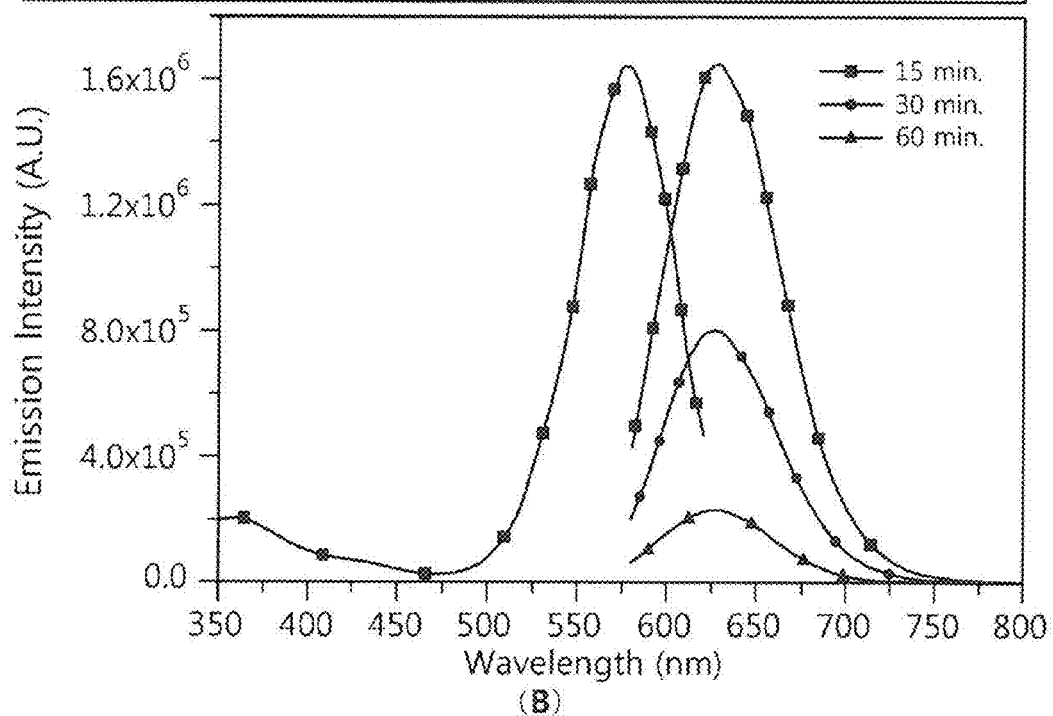

SEQUENCE LISTING

```
<160> NUMBER OF SEQ ID NOS: 16

<210> SEQ ID NO 1
<211> LENGTH: 12
<212> TYPE: DNA
<213> ORGANISM: Artificial Sequence
<220> FEATURE:
<223> OTHER INFORMATION: X region 1

<400> SEQUENCE: 1
cctccttcct cc                                                          12

<210> SEQ ID NO 2
<211> LENGTH: 12
<212> TYPE: DNA
<213> ORGANISM: Artificial Sequence
<220> FEATURE:
<223> OTHER INFORMATION: X region 2

<400> SEQUENCE: 2
ccctttaacc cc                                                          12

<210> SEQ ID NO 3
<211> LENGTH: 12
```

```
<212> TYPE: DNA
<213> ORGANISM: Artificial Sequence
<220> FEATURE:
<223> OTHER INFORMATION: X region 3

<400> SEQUENCE: 3
ccctcttaac cc                                                       12

<210> SEQ ID NO 4
<211> LENGTH: 12
<212> TYPE: DNA
<213> ORGANISM: Artificial Sequence
<220> FEATURE:
<223> OTHER INFORMATION: X region 4

<400> SEQUENCE: 4
cccttaatcc cc                                                       12

<210> SEQ ID NO 5
<211> LENGTH: 12
<212> TYPE: DNA
<213> ORGANISM: Artificial Sequence
<220> FEATURE:
<223> OTHER INFORMATION: X region 5

<400> SEQUENCE: 5
ccctaactcc cc                                                       12

<210> SEQ ID NO 6
<211> LENGTH: 21
<212> TYPE: DNA
<213> ORGANISM: Artificial Sequence
<220> FEATURE:
<223> OTHER INFORMATION: Y region

<400> SEQUENCE: 6
tggcatacag ggagccaggc a                                             21

<210> SEQ ID NO 7
<211> LENGTH: 33
<212> TYPE: DNA
<213> ORGANISM: Artificial Sequence
<220> FEATURE:
<223> OTHER INFORMATION: Silver nanocluster probe 1

<400> SEQUENCE: 7
cctccttcct cctggcatac agggagccag gca                                33

<210> SEQ ID NO 8
<211> LENGTH: 33
<212> TYPE: DNA
<213> ORGANISM: Artificial Sequence
<220> FEATURE:
<223> OTHER INFORMATION: Silver nanocluster probe 2

<400> SEQUENCE: 8
cccttTaacc cctggcatac agggagccag gca                                33

<210> SEQ ID NO 9
<211> LENGTH: 33
<212> TYPE: DNA
<213> ORGANISM: Artificial Sequence
<220> FEATURE:
<223> OTHER INFORMATION: Silver nanocluster probe 3

<400> SEQUENCE: 9
```

-continued

```
ccctcttaac cctggcatac agggagccag gca                    33
```

<210> SEQ ID NO 10
<211> LENGTH: 33
<212> TYPE: DNA
<213> ORGANISM: Artificial Sequence
<220> FEATURE:
<223> OTHER INFORMATION: Silver nanocluster probe 4

<400> SEQUENCE: 10

```
cccttaatcc cctggcatac agggagccag gca                    33
```

<210> SEQ ID NO 11
<211> LENGTH: 33
<212> TYPE: DNA
<213> ORGANISM: Artificial Sequence
<220> FEATURE:
<223> OTHER INFORMATION: Silver nanocluster probe 5

<400> SEQUENCE: 11

```
ccctaactcc cctggcatac agggagccag gca                    33
```

<210> SEQ ID NO 12
<211> LENGTH: 21
<212> TYPE: RNA
<213> ORGANISM: Artificial Sequence
<220> FEATURE:
<223> OTHER INFORMATION: RNA-miR160

<400> SEQUENCE: 12

```
ugccuggcuc ccuguaugcc a                                 21
```

<210> SEQ ID NO 13
<211> LENGTH: 24
<212> TYPE: RNA
<213> ORGANISM: Artificial Sequence
<220> FEATURE:
<223> OTHER INFORMATION: RNA-miR163

<400> SEQUENCE: 13

```
uugaagagga cuuggaacuu cgau                              24
```

<210> SEQ ID NO 14
<211> LENGTH: 21
<212> TYPE: RNA
<213> ORGANISM: Artificial Sequence
<220> FEATURE:
<223> OTHER INFORMATION: RNA-miR166

<400> SEQUENCE: 14

```
ucggaccagg cuucauuccc c                                 21
```

<210> SEQ ID NO 15
<211> LENGTH: 21
<212> TYPE: RNA
<213> ORGANISM: Artificial Sequence
<220> FEATURE:
<223> OTHER INFORMATION: RNA-miR172

<400> SEQUENCE: 15

```
agaaucuuga ugaugcugca u                                 21
```

<210> SEQ ID NO 16
<211> LENGTH: 23
<212> TYPE: RNA
<213> ORGANISM: Artificial Sequence

```
<220> FEATURE:
<223> OTHER INFORMATION: RNA-RY-1

<400> SEQUENCE: 16
gccagcgcuc gguuuuuuuu uuu                                              23
```

SILVER NANOCLUSTER PROBE AND TARGET POLYNUCLEOTIDE DETECTION METHOD USING SAME, AND SILVER NANOCLUSTER PROBE DESIGN METHOD

CROSS-REFERENCE TO RELATED APPLICATIONS his application is a §371 of PCT/KR2012/006659 filed on Aug. 22, 2012, which claims the benefit of Korean Patent Application No. 10-2012-0091554 filed on Aug. 22, 2012, the contents of each of which are incorporated herein by reference.

TECHNICAL FIELD

The present invention relates to a silver nanocluster probe and a method for designing the same, and more particularly, to a silver nanocluster probe and a method for designing the same, in which the silver nanocluster probe comprises a silver nanoparticle binding region and a specific nucleotide sequence region that specifically binds to a target polynucleotide, wherein the silver nanocluster probe is configured such that it will emit detectable light when silver nanoparticles bind to the silver nanoparticle binding region to form a silver nanocluster, but light emission from the silver nanocluster probe will decrease or decay when the target polynucleotide binds to the specific nucleotide sequence region.

The present invention also relates to a method of detecting either the presence of a target polynucleotide in a sample or a mutation in the target polynucleotide by determining that light emission decreases or decays when the target polynucleotide binds to the specific nucleotide sequence region of a silver nanocluster probe that emits detectable light.

Moreover, the present invention relates to a novel method of detecting a target polynucleotide, which can rapidly and conveniently detect either the presence of the target polynucleotide in a sample or a mutation in the target polynucleotide by using the above-described silver nanocluster probe while satisfying both the specificity and sensitivity of detection.

Additionally, the present invention relates to a method of detecting either the presence of a target polynucleotide or a mutation in the target polynucleotide based on a decrease or decay in the emission of light at a wavelength of interest, by providing various kinds of silver nanocluster probes that emit light at various wavelengths, and providing the silver nanocluster probes as sensors corresponding to various target polynucleotides.

BACKGROUND ART

Biosensors are devices that can automatically analyze large amounts of gene and protein informations or that can analyze the presence or absence and the function of a physiologically active substance in a relatively simple and rapid manner. Thus, biosensors have been actively applied in various fields, including gene and protein research field, medical field, agricultural, food, environmental and chemical industries, etc. For example, a microarray chip, which is a type of biosensor, is fabricated by immobilizing a probe(s) specific for a target polynucleotide(s) on a glass slide, using a microarray equipment. When it is used, the presence or absence of the target polynucleotide in a sample and a mutation in the sequence of the target polynucleotide can be analyzed by amplifying the target polynucleotide using fluorescence-labeled specific primers, hybridizing the amplification product to the microarray chip and analyzing the fluorescence signal with a scanner.

A microfluidics chip is another type of biosensor. When it is used, whether a trace analyte (DNA, RNA, peptide, protein, etc.) reacts in the chip is analyzed while the trace analyte is allowed to flow into the chamber of the chip. When this microfluidics chip is used, whether the analyte reacts in the chip can be determined by detection of an electrical signal in a relatively simple and quick manner compared to the use of the above-described microarray chip. Thus, the microfluidics chip is highly useful in the medical diagnostic field. Particularly, the microfluidics chip is advantageous from the viewpoint of the miniaturization of the system and the convenience of detection, because it can detect the reaction of the analyte using an electrical signal, not a fluorescence signal. However, this microfluidics chip is problematic in terms of the reproducibility of detection due to a buffer that is received in the reaction chamber. It also has a problem in that a sweeping process for applying an alternating current at each frequency is required, making it inconvenient to measure an impedance value, resulting in difficulty in analysis. Thus, in the biosensor field, there is still a need for a novel sensing-based technology that satisfies both specificity and sensitivity while detecting an analyte in a rapid and convenient manner, and a novel sensor based on this technology.

Meanwhile, with the recent development of nanotechnology, technologies based on gold nanoparticles or silver nanoparticles have been developed. For example, Korean Patent No. 10-0981987 discloses a technology that maximizes sensitivity by amplifying a signal through staining of silver nanoparticles when nano-sized arrays, which are difficult to analyze by a conventional fluorescence-based detection method, are analyzed using a scanning tunneling microscope (STM).

In addition, a fluorophore such as Cy3 or Cy5, which is used in the microarray chip as described above, is inconvenient in that it should be previously labeled onto oligonucleotide primers. In addition, it has problems such as poor optical stability and insufficient light intensity. In an attempt to overcome these problems, fluorophores based on clusters of (oligonucleotide-stabilized silver nanoparticles were proposed (Chris I. Richards et al., Oligonucleotide-Stabilized Ag Nanocluster Fluorophores, J. AM. CHEM. SOC. 2008, 130, 5038-5039).

In addition, a technology that uses silver nanoparticle clusters in the labeling of reporter oligonucleotides produced in target-assisted isothermal exponential amplification (TAIEA) was also reported (Yu-Qiang Liu et al., Attomolar Ultrasensitive MicroRNA Detection by DNA-Scaffolded Silver-Nanocluster Probe Based on Isothermal Amplification, Anal. Chem., May 29, 2012, A-E). In this prior technology, if miRNA is present when TAIEA is performed, it is annealed and amplified, and at that time, a reporter oligonucleotide that indicates the amplification and presence of the target miRNA is produced in addition to an oligonucleotide complementary to the target miRNA, and thus the target miRNA is detected by the detection of the labeled reporter oligonucleotide. In this prior technology, in order to solve problems such as the inhibition of amplification, the induction of nonspecific amplification and the problem in detection sensitivity, which occur when the reporter oligonucleotide is labeled with a Cy5 fluorophore, the reporter oligonucleotide is labeled with a cluster of silver nanoparticles.

However, the prior art technologies as described above relate to either amplifying a signal for electron microscopic observation using silver nanoparticles as an electron microscopic dye or labeling an oligonucleotide with a cluster of silver nanoparticles in place of the fluorophore Cy3 or Cy5, and are far from a new base technology that rapidly and conveniently detects either the presence of a target polynucleotide in a sample or a mutation in the polynucleotide while satisfying both the specificity and sensitivity of detection.

Accordingly, the present inventors have conducted extensive studies to solve the above-described problems occurring in the prior art and to develop a novel detection-based technology that rapidly and conveniently detects either the presence of a target polynucleotide in a sample or a mutation in the polynucleotide while satisfying both the specificity and sensitivity of detection. As a result, the present inventors have found that a silver nanocluster probe comprising a silver nanoparticle binding region and a specific nucleotide sequence region that specifically binds to a target polynucleotide can show stronger emission intensity than conventional silver nanoparticle clusters when silver nanoparticles bind to the silver nanoparticle binding region, and light emission from the silver nanocluster probe will decrease or decay when the target polynucleotide binds to the specific nucleotide sequence region, thereby completing the present invention.

SUMMARY OF INVENTION

It is an object of the present invention to provide a silver nanocluster probe and a method for designing the same, in which the silver nanocluster probe comprises a silver nanoparticle binding region and a specific nucleotide sequence region that specifically binds to a target polynucleotide, wherein the silver nanocluster probe is configured such that it will emit detectable light when silver nanoparticles bind to the silver nanoparticle binding region to form a silver nanocluster, but light emission from the silver nanocluster probe will decrease or decay when the target polynucleotide binds to the specific nucleotide sequence region.

Another object of the present invention is to provide a method of detecting either the presence of a target polynucleotide in a sample or a mutation in the target polynucleotide by determining that light emission decreases or decays when the target polynucleotide binds to the specific nucleotide sequence region of a silver nanocluster probe that emits detectable light.

Still another object of the present invention is to provide a method of detecting either the presence of a target polynucleotide or a mutation in the target polynucleotide based on a decrease or decay in the emission of light at a wavelength of interest, by providing various kinds of silver nanocluster probes that emit light at various wavelengths, and providing the silver nanocluster probes as sensors corresponding to various target polynucleotides.

Accordingly, an object of the present invention is to provide a novel method of detecting a target polynucleotide, which can rapidly and conveniently detect either the presence of the target polynucleotide in a sample or a mutation in the target polynucleotide by using the above-described silver nanocluster probe while satisfying both the specificity and sensitivity of detection.

DETAILED DESCRIPTION OF INVENTION

In order to accomplish the above objects, the present invention provides a silver nanocluster probe which comprises a silver nanoparticle binding region and a specific nucleotide sequence region that specifically binds to a target polynucleotide, wherein the silver nanocluster probe is configured such that it will emit detectable light when silver nanoparticles bind to the silver nanoparticle binding region to form a silver nanocluster, but light emission from the silver nanocluster probe will decrease or decay when the target polynucleotide binds to the specific nucleotide sequence region.

Terms used herein are defined as follows.

As used herein, the term "target polynucleotide" refers to a single- or double-stranded DNA or RNA to be detected in a sample. Examples of the target polynucleotide include a polynucleotide having a specific nucleotide sequence region, which is used in single nucleotide polymorphism analysis or genotype analysis, a marker polynucleotide that is used in the diagnosis of a specific disease, a polynucleotide having a genetically significant mutation, miRNA, mRNA and non-coding RNA.

In an example of the present invention, a silver nanocluster probe was used to detect miRNA, but miRNA should be understood as an example of a target polynucleotide. In addition, it is to be understood that a silver nanocluster probe according to the present invention, a method for designing the same, and a method for detecting a target polynucleotide using the silver nanocluster probe are flatform technologies capable of detecting either the presence of various target polynucleotides or a mutation in the target polynucleotides.

The present invention provides a silver nanocluster probe having the following structural formula 1 and specifically binding to a target polynucleotide:

$$X\text{-}5'\text{-}Y\text{-}3' \text{ or } 5'\text{-}Y\text{-}3'\text{-}X \hspace{2cm} \text{Structural Formula 1}$$

wherein X is a silver nanoparticle binding region, the silver nanoparticle binding region being allowed to be bound to silver nanoparticles and to form a silver nanocluster together with the silver nanoparticles;

Y is an oligonucleotide comprising a specific nucleotide sequence region, the specific nucleotide sequence region being allowed to be specifically bound to a target polynucleotide, and the 5' or 3' end of Y being linked to X of structural formula 1; and wherein the silver nanocluster probe emits detectable light when the silver nanoparticles bind to the silver nanoparticle binding region X and form the silver nanocluster, but the light emission from the silver nanocluster probe decreases or decays when the target polynucleotide binds to the specific nucleotide sequence region Y.

In the silver nanocluster probe according to an embodiment of the present invention, X may be a scaffold selected from the group consisting of nucleic acids (e.g., DNA, RNA, etc.), proteins, polymers, dendrimers, organic compounds and inorganic matrices. For example, when X is DNA, X may be an oligonucleotide selected from the group consisting of SEQ ID NOs: 1 to 5.

In the silver nanocluster probe according to an embodiment of the present invention, the target polynucleotide may be miRNA 160, and Y may be an oligonucleotide of SEQ ID NO: 6. For reference, miRNA 160 is an miRNA that targets the transcription of an auxin response factor that is important for signaling of the plant growth hormone, auxin in *Arabidopsis*.

In the silver nanocluster probe according to an embodiment of the present invention, when Y is the oligonucleotide of SEQ ID NO: 6, the probe of structural formula 1 may be an oligonucleotide selected from the group consisting of SEQ ID NOs: 7 to 11.

A method for detecting a target polynucleotide using a silver nanocluster probe according to the present invention comprises the steps of:

(a) preparing a silver nanocluster probe that has the following structural formula 1 and that specifically binds to a target polynucleotide:

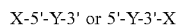   Structural Formula 1

(b) allowing the target polynucleotide to bind complementarily to Y of structural formula 1, Y being an oligonucleotide comprising a specific nucleotide sequence region that is specifically bound to the target polynucleotide, and the 5' or 3' end of Y being linked to X of structural formula 1;

(c) binding silver nanoparticles to X of structural formula 1 that is a silver nanoparticle binding region, the silver nanoparticle binding region forming a silver nanocluster together with the silver nanoparticles; and (d) determining that the intensity of light emitted from the silver nanocluster formed by the binding of the silver nanoparticles to X of structural formula 1 decreases or decays, according to the binding of the target polynucleotide to Y of structural formula 1.

The method for detecting the target polynucleotide according to an embodiment of the present invention may further comprise a step of quantifying a decrease in the intensity of the emitted light and quantifying the target polynucleotide based on $I_0/I$, wherein $I_0$ is the intensity of the light emitted from the silver nanocluster formed by the binding of the silver nanoparticles to X of structural formula 1 when the target polynucleotide is not present, and I is the intensity of the light determined to decrease or decay in step (d).

The method for detecting the target polynucleotide according to an embodiment of the present invention further comprises a step of detecting either the presence of the target polynucleotide in a sample or a mutation in the target polynucleotide by determining whether the intensity of the light decreases or decays.

The method for detecting the target polynucleotide according to an embodiment of the present invention, X of structural formula 1 may be a scaffold selected from the group consisting of nucleic acids (e.g., DNA, RNA, etc.), proteins, polymers, dendrimers, organic compounds and inorganic matrices. For example, when X is DNA, X may be an oligonucleotide selected from the group consisting of SEQ ID NOs: 1 to 5.

The method for detecting the target polynucleotide according to an embodiment of the present invention, step (c) may be performed by the addition of AgNO₃ and reduction with NaBH₄.

The method for detecting the target polynucleotide according to an embodiment of the present invention, the target polynucleotide may be miRNA 160, and Y may be an oligonucleotide of SEQ ID NO: 6.

In the method for detecting the target polynucleotide according to an embodiment of the present invention, when Y is the oligonucleotide of SEQ ID NO: 6, the probe of structural formula 1 may be an oligonucleotide selected from the group consisting of SEQ ID NOs: 7 to 11.

A method for designing a silver nanocluster probe having the following structural formula 1 and specifically binding to a target polynucleotide, according to the present invention, comprises the steps of:

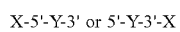   Structural Formula 1 constructing X of structural formula 1 that is a silver nanoparticle binding region, the silver nanoparticle binding region being allowed to be bound to silver nanoparticles and to form a silver nanocluster together with the silver nanoparticles;

constructing Y of structural formula 1 that is an oligonucleotide comprising a specific nucleotide sequence region, the specific nucleotide sequence region being allowed to be specifically bound to a target polynucleotide, and the 5' or 3' end of Y being linked to X of structural formula 1; and wherein the designed silver nanocluster probe emits detectable light when silver nanoparticles bind to the silver nanoparticle binding region X and form the silver nanocluster, but the light emission from the silver nanocluster probe decreases or decays when the target polynucleotide binds to the specific nucleotide sequence region Y.

In the method for designing the silver nanocluster probe according to an embodiment of the present invention, X of structural formula 1 may be a scaffold selected from the group consisting of nucleic acids (e.g., DNA, RNA, etc.), proteins, polymers, dendrimers, organic compounds and inorganic matrices. For example, when X is DNA, X may be an oligonucleotide selected from the group consisting of SEQ ID NOs: 1 to 5.

In the method for designing the silver nanocluster probe according to an embodiment of the present invention, the target polynucleotide may be miRNA 160, and Y may be an oligonucleotide of SEQ ID NO: 6.

In the method for designing the silver nanocluster probe according to an embodiment of the present invention, when Y is the oligonucleotide of SEQ ID NO: 6, the probe of structural formula 1 may be an oligonucleotide selected from the group consisting of SEQ ID NOs: 7 to 11.

In the present invention, the emitted light preferably has a wavelength from red to infrared wavelength range, and more preferably a wavelength of between 600 nm and 750 nm.

Advantageous Effects

The silver nanocluster probe according to the present invention comprises a silver nanoparticle binding region and a specific nucleotide sequence region that specifically binds to a target polynucleotide. The silver nanocluster probe according to the present invention is constructed such that it will emit detectable light when silver nanoparticles bind to the silver nanoparticle binding region to form a silver nanocluster, but the light emission from the silver nanocluster probe will decrease or decay when the target polynucleotide binds to the specific nucleotide sequence region.

According to the present invention, either the presence of a target polynucleotide in a sample or a mutation in the target polynucleotide can be detected in a rapid and convenient manner by determining whether light emission decreases or decays when the target polynucleotide binds to the specific nucleotide sequence region of the silver nanocluster probe that emits detectable light. Specifically, when the silver nanocluster probe according to the present invention is used, either the presence of a target polynucleotide in a sample or a mutation in the target polynucleotide can be rapidly and conveniently detected within 1 hour without a separate labeling process while satisfying both the specificity and sensitivity of detection.

In addition, the present invention provides various silver nanocluster probes emitting light at various wavelengths, and these silver nanocluster probes can be provided as sensors corresponding to various target polynucleotides.

Thus, the present invention can provide a biosensor capable of detecting either the presence of a target polynucleotide or a mutation in the target polynucleotide based on whether the emission of light at the wavelength of interest decreases or decays.

BRIEF DESCRIPTION OF DRAWINGS

FIG. 2 shows the nucleotide sequence of a silver nanocluster probe (DNA-12nt-RED-160 probe) according to an embodiment of the present invention, and shows the change in emission intensity over time when silver nanoparticles bind to the silver nanocluster probe.

EXAMPLES

Hereinafter, the present invention will be described with reference to non-limiting examples. It is to be understood, however, that these examples are for illustrative purposes only and are not intended to limit the scope of the present invention. Thus, those that can be easily contemplated by persons skilled in the art from the detailed description and examples of the present invention are interpreted to fall within the scope of the present invention. References cited herein are incorporated herein by reference.

Example 1: Construction of a Silver Nanocluster Probe and Analysis of its Emission A nucleotide sequence (SEQ ID NO: 6; hereinafter abbreviated as "DNA-160") complementary to miRNA 160 (SEQ ID NO: 12; hereinafter abbreviated as "miR160") was added to the 3' end of an oligonucleotide (SEQ ID NO: 1; hereinafter abbreviated as "DNA-12nt-RED") of a silver nanoparticle binding region (region X), thereby constructing a silver nanocluster probe (SEQ ID NO: 7; hereinafter referred to as "DNA-12nt-RED-160 probe") according to an embodiment of the present invention (see FIG. 2(A)). In this Example, the oligonucleotide of SEQ ID NO: 1 for region X, which emits red light when silver nanoparticles bind thereto, was linked to the specific nucleotide sequence region (region Y) that specifically binds to a target polynucleotide, but the present invention is not limited thereto. Various oligonucleotides capable of emitting light at various wavelengths can be used for region X. For example, the oligonucleotide of region X may be any one of SEQ ID NOs: 1 to 5, and the oligonucleotide of region Y may include a nucleotide sequence of SEQ ID NO: 6.

Examples of Oligonucleotide of Region X

Red emission:
(SEQ ID NO: 1)
5'-CCTCCTTCCTCC-3';

blue emission:
(SEQ ID NO: 2)
5'-CCCTTTAACCCC-3';

green emission:
(SEQ ID NO: 3)
5'-CCCTCTTAACCC-3';

Yellow emission:
(SEQ ID NO: 4)
5'-CCCTTAATCCCC-3';

Near infrared emission:
(SEQ ID NO: 5)
5'-CCCTAACTCCCC-3'.

Oligonucleotide of Region Y (SEQ ID NO: 6)
5'-TGGCATACAGGGAGCCAGGCA-3'.

Examples of Silver Nanocluster Probe Composed of Region X and Region Y

```
                                            (SEQ ID NO: 7)
5'-CCTCCTTCCTCCTGGCATACAGGGAGCCAGGCA-3';

(SEQ ID NO: 8)
5'-CCCTTTAACCCCTGGCATACAGGGAGCCAGGCA-3';

(SEQ ID NO: 9)
5'-CCCTCTTAACCCTGGCATACAGGGAGCCAGGCA-3';

(SEQ ID NO: 10)
5'-CCCTTAATCCCCTGGCATACAGGGAGCCAGGCA-3';

(SEQ ID NO: 11)
5'-CCCTAACTCCCCTGGCATACAGGGAGCCAGGCA-3'.
```

Figure 1:
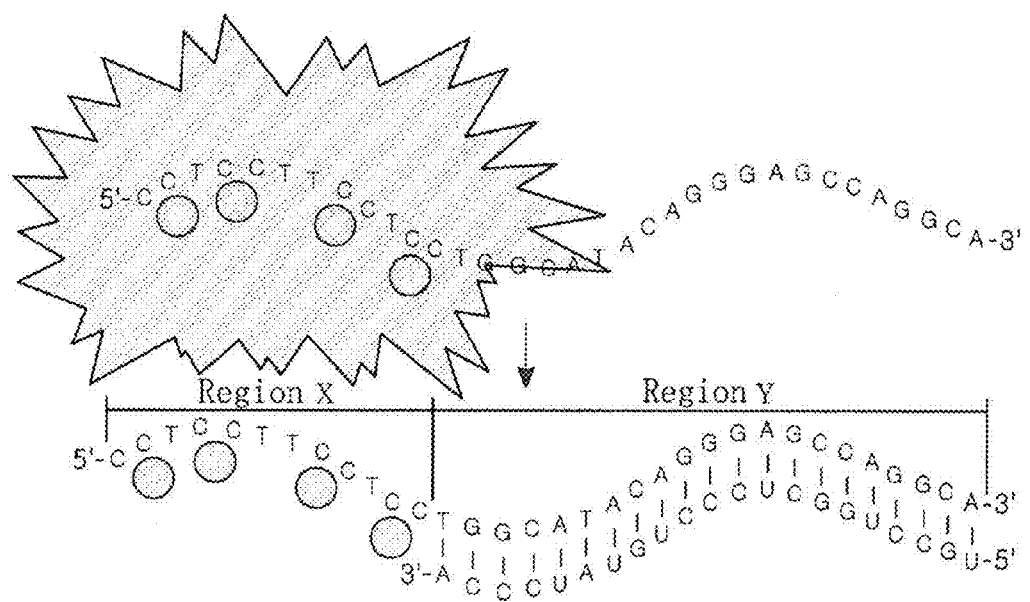
FIG. 1 shows that detectable light is emitted when silver nanoparticles bind to the silver nanoparticle binding region of a silver nanocluster probe according to the present invention, but light emission decreases or decays when a target polynucleotide binds to the specific nucleotide sequence region of the silver nanocluster probe.

The target oligonucleotide miRNA 160 used in this Example is known to target the transcription of an auxin response factor that is important for signaling of the plant growth hormone, auxin in *Arabidopsis*. To prepare the silver nanocluster probe of the present invention that emits light, an oligonucleotide of SEQ ID NO: 7 (15 μM) was allowed to stand at 25° C. for 10 minutes, and then 250 μM AgNO$_3$ and 250 μM NaBH$_4$ were added thereto at a ratio of 1:17:17 (oligonucleotide:AgNO$_3$:NaBH$_4$) to a final volume of 50 μL (see FIG. 1). AgNO$_3$ (99.9999%) and NaBH$_4$ (99.99%) used were purchased from Sigma Aldrich. Then, emission spectra of 1.5 μM of the resulting silver nanocluster probe (DNA-12nt-RED-160 probe) were measured and recorded. The emission spectra were measured and recorded by a fluorimeter (Horiba Jobin Yvon, Fluoromax-4) in a 1 mm quartz cuvette. As a result, the silver nanocluster probe (DNA-12nt-RED-160 probe) of the present invention prepared in this Example showed strong red emission when silver nanoparticles formed clusters (see FIG. 2(B)).

Figure 3:
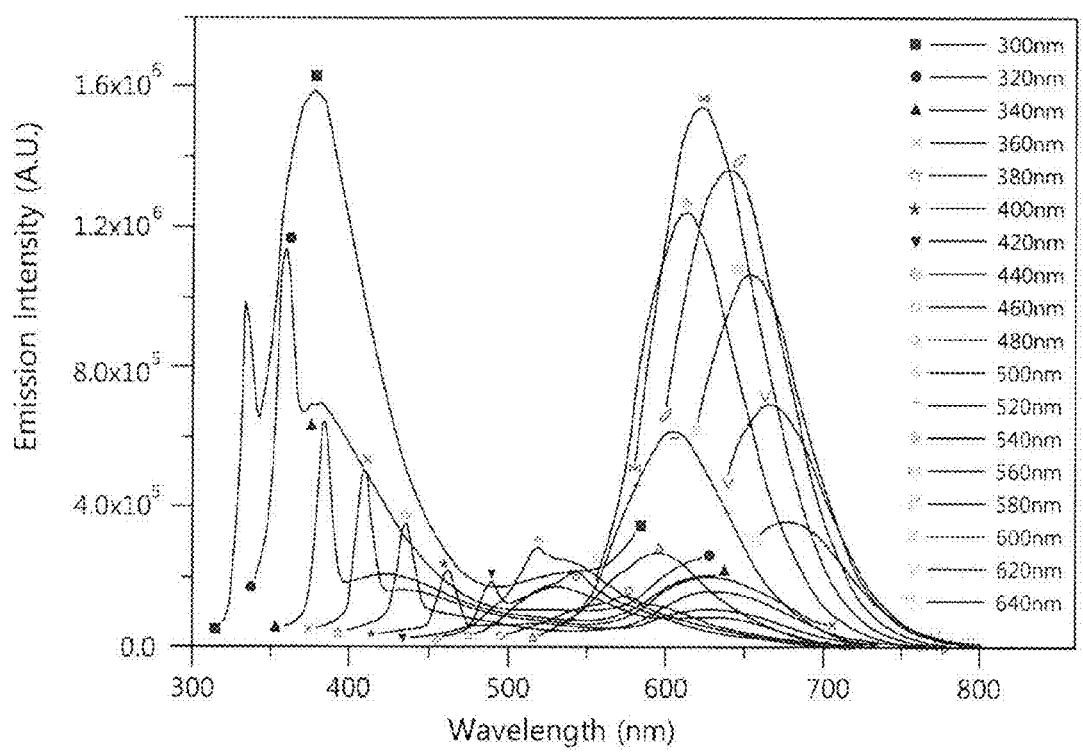
FIG. 3 shows emission spectra measured as a function of an excitation wavelength of 300-640 nm at 1 hour after the addition of $AgNO_3$ and reduction with $NaBH_4$ for a silver 1.3 nanocluster probe (DNA-12nt-RED-160 probe) according to an embodiment of the present invention.
Figure 4:
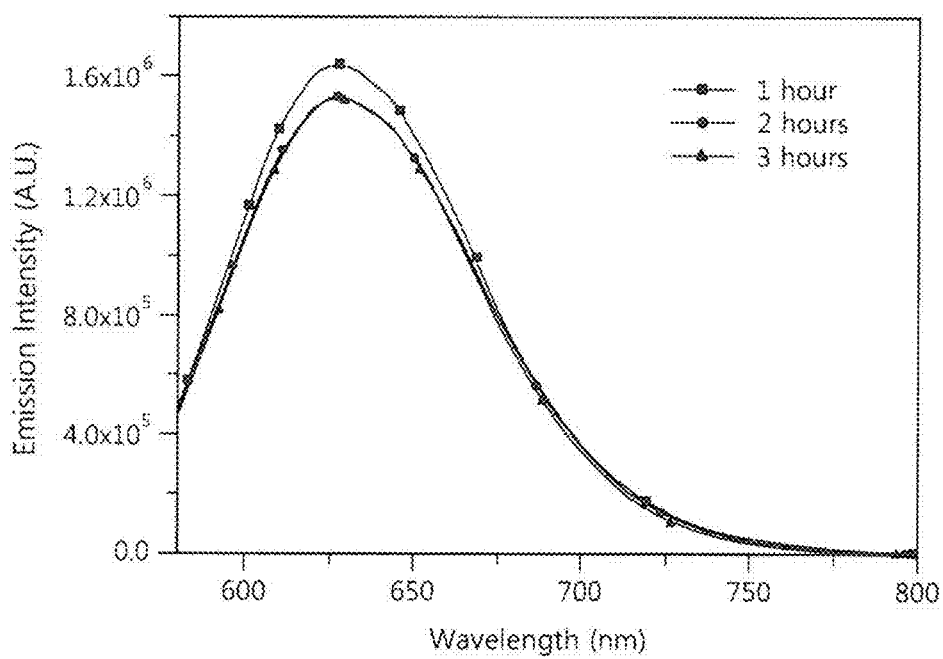
FIG. 4 shows emission spectra at 1, 2 and 3 hours after the addition of $AgNO_3$ and reduction with $NaBH_4$ for a silver nanocluster probe (DNA-12nt-RED-160 probe) according to an embodiment of the present invention, indicating that the change in the emission intensity is not large and the emission intensity is stable.
Figure 5:
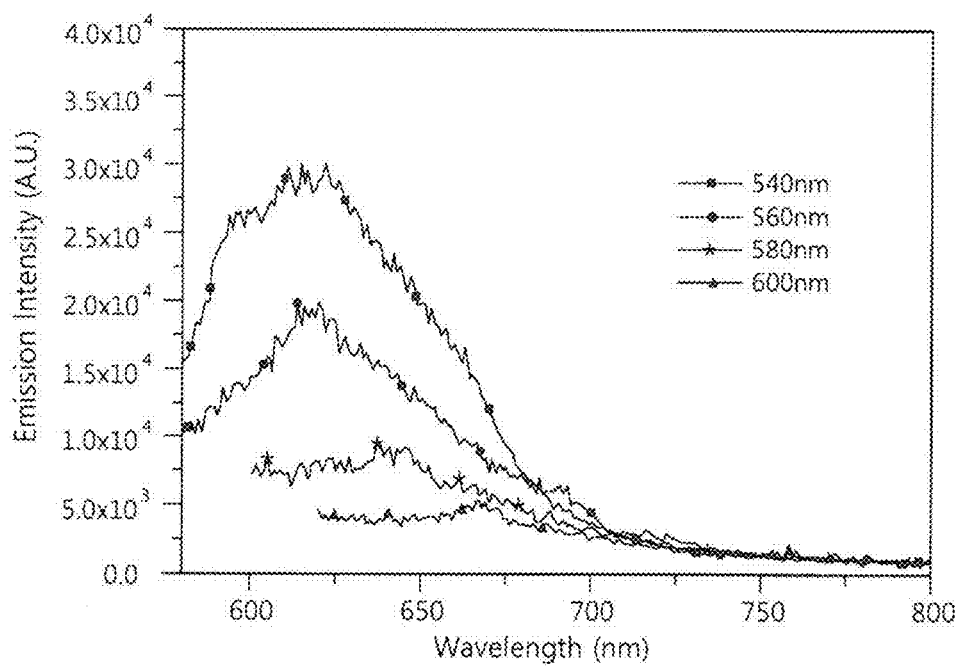
FIG. 5 shows emission spectra measured as a function of an excitation wavelength of 540-600 nm at 1 hour after the addition of $AgNO_3$ and reduction with $NaBH_4$ for conventional DNA-12nt-RED sequence.
Figure 6:
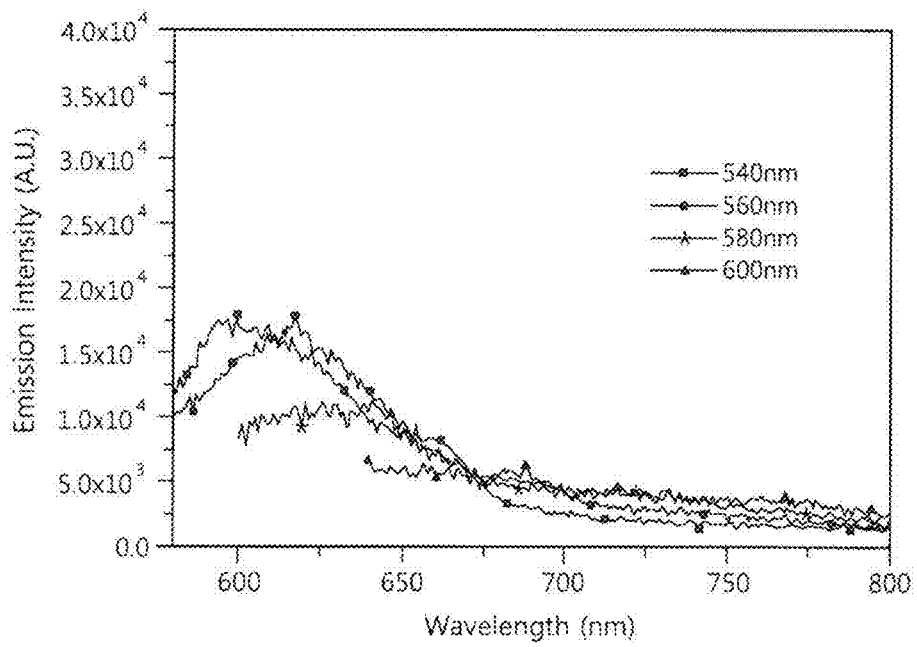
FIG. 6 shows emission spectra measured as a function of an excitation wavelength of 540-600 nm at 1 hour after the addition of $AgNO_3$ and reduction with $NaBH_4$ for DNA-160 sequence alone.

FIG. 2(B) shows emission spectra obtained by the addition of AgNO$_3$ and reduction with NaBH$_3$ for 1.5 μM of the DNA-12nt-RED-160 probe according to an embodiment of the present invention, followed by the excitation at 560 nm, and then the measuring of emission at 620 nm, and shows the change in emission intensity over time (at 15 min, 30 min. and 60 min). Further, emission spectra were measured and recorded as a function of an excitation wavelength of 300-640 nm at 1 hour after the addition of AgNO$_3$ and reduction with NaBH$_4$ for 1.5 μM of the DNA-12nt-RED-160 probe according to an embodiment of the present invention (FIG. 3). As can be seen from the results in FIG. 2(B), the DNA-12nt-RED-160 probe showed its emission (within 1 hour) faster than the DNA-12nt-RED sequence alone, and the emission intensity of the DNA-12nt-RED-160 probe was 100 times higher than the DNA-12nt-RED at 1 hour after the addition of AgNO$_3$ and reduction with NaBH$_4$. Also, the DNA-12nt-RED-160 probe showed no significant change in its emission intensity at 1, 2 and 3 hours after the addition of AgNO$_3$ and reduction with NaBH$_4$, confirming its stable emission property (see FIG. 4). However, when emission spectra were measured for 1.5 μM of the DNA-12nt-RED sequence alone or 1.5 μM of the DNA-160 sequence alone as a function of an excitation wavelength of 540-600 nm at 1 hour after the addition of AgNO$_3$ and reduction with NaBH$_4$, it was shown that the emission intensity of the sequences was lower than that of the silver nanocluster probe (DNA-12nt-RED-160 probe), and the sequences required several hours for red emission (see FIGS. 5 and 6).

In addition, for each of the DNA-12nt-RED-160 probe, the DNA-12nt-RED sequence and the miR160-specific DNA-160 sequence, the time required for red emission and the emission intensity at 620 nm were measured after excitation at 560 nm following the addition of AgNO$_3$ and reduction with NaBH$_4$. The results of the measurement are shown in Table 1 as below. To form silver nanoparticle clusters, AgNO$_3$ and NaBH$_4$ were added to the DNA-12nt-RED sequence (150 μM and 15 μM in 50 μL) at a ratio of 1:6:6 (DNA-12nt-RED sequence:AgNO$_3$:NaBH$_4$) to a final volume of 50 μL, and AgNO$_3$ and NaBH$_4$ were added to the DNA-160 sequence (15 μM in 50 μL) at a ratio of 1:17:17 (DNA-160 sequence:AgNO$_3$:NaBH$_4$) to a final volume of 50 μL. The volume was increased from 50 μL to 500 μL before measurement of the emission intensity. Meanwhile, the aforesaid ratios of DNA:AgNO$_3$:NaBH$_4$ were different because the lengths of the DNAs, to which silver nanoparticles bind, were different. In this Example, the ratio of DNA:AgNO$_3$:NaB$_3$H$_4$ was determined in such a manner that the ratio of 1:2 (Ag$^+$ ion:nucleotides) is obtained.

TABLE 1

Comparison of the emission intensity and the time required for red emission for each of DNA-12nt-RED-160 probe, DNA-12nt-RED sequence and DNA-160 sequence

| Sequence | Conc. | Ratio | Int. at 620 nm | Time |
|---|---|---|---|---|
| DNA-12nt-RED-160 probe | 1.5 μM | 1:17:17 | 1.60E+06 | 1 h. |
| DNA-160 | 1.5 μM | 1:17:17 | 1.70E+04 | 1 h. |
| DNA-160 | 1.5 μM | 1:17:17 | 2.40E+04 | 3 h. |
| DNA-160 | 1.5 μM | 1:17:17 | 4.60E+04 | 6 h. |
| DNA-12nt-RED | 1.5 μM | 1:6:6 | 2.00E+04 | 1 h. |
| DNA-12nt-RED | 1.5 μM | 1:6:6 | 3.50E+04 | 3 h. |
| DNA-12nt-RED | 1.5 μM | 1:6:6 | 4.80E+04 | 6 h. |
| DNA-12nt-RED | 15 μM | 1:6:6 | 1.61E+05 | 1 h. |
| DNA-12nt-RED | 15 μM | 1:6:6 | 3.55E+05 | 3 h. |
| DNA-12nt-RED | 15 μM | 1:6:6 | 4.70E+05 | 6 h. |

As can be seen from the above-described experimental results, the silver nanocluster probe, comprising the silver nanoparticle binding region and the specific nucleotide sequence region that specifically binds to a target polynucleotide, showed its emission (within 1 hour) faster than the silver nanoparticle binding region (DNA-12nt-RED sequence) alone or the specific nucleotide sequence region (DNA-160 sequence) alone, and showed its stable emission property even with the passage of time. Particularly, the results showed an unexpected effect that the emission intensity of the silver nanocluster probe was 100 times higher than the sequence alone. Thus, it can be seen that the silver nanocluster probe of the present invention, which comprises the silver nanoparticle binding region and the specific nucleotide sequence region that specifically binds to a target polynucleotide, is suitable for rapid detection and can increase the sensitivity and accuracy of detection.

Example 2: Examination of the Ability of the Silver Nanocluster Probe to Detect a Target Polynucleotide by its Specific Binding A mixture (final volume: 50 μL) of the silver nanocluster probe (1.5 μM; DNA-12nt-RED-160 probe) prepared in Example 1 and miR160 (target polynucleotide; SEQ ID NO: 12) in the concentration from 0 μM to 1.5 μM was incubated at 25° C. for 15 minutes. In the same manner as described in Example 1, AgNO$_3$ and NaBH$_4$ were added to the incubated mixture, followed by incubation at 25° C. for 1 hour. Then, 450 μL of distilled water was added thereto, and emission spectra were measured and recorded at 620 nm (after excitation at 560 nm) by a fluorimeter (Horiba Jobin Yvon, Fluoromax-4) in a 1 mm quartz cuvette (see FIG. 7(A)). As can be seen from the results in FIG. 7(A), the red emission intensity of the silver nanocluster probe (DNA-12nt-RED-160 probe) decreased depending on the concentration of the target polynucleotide miR160. In other words, it was shown that the amount of DNA-12nt-RED-160 probe specifically bound to the target polynucleotide miR160 increased with an increase in the concentration of miR160, and thus the red emission intensity gradually decreased or decayed. Thus, the silver nanocluster probe of the present invention can be used as a probe and a sensor comprising the same that can detect either the presence of a target polynucleotide or a mutation in the target polynucleotide by quantifying the decrease in red emission signal, caused by the presence of the target polynucleotide.

Figure 7:
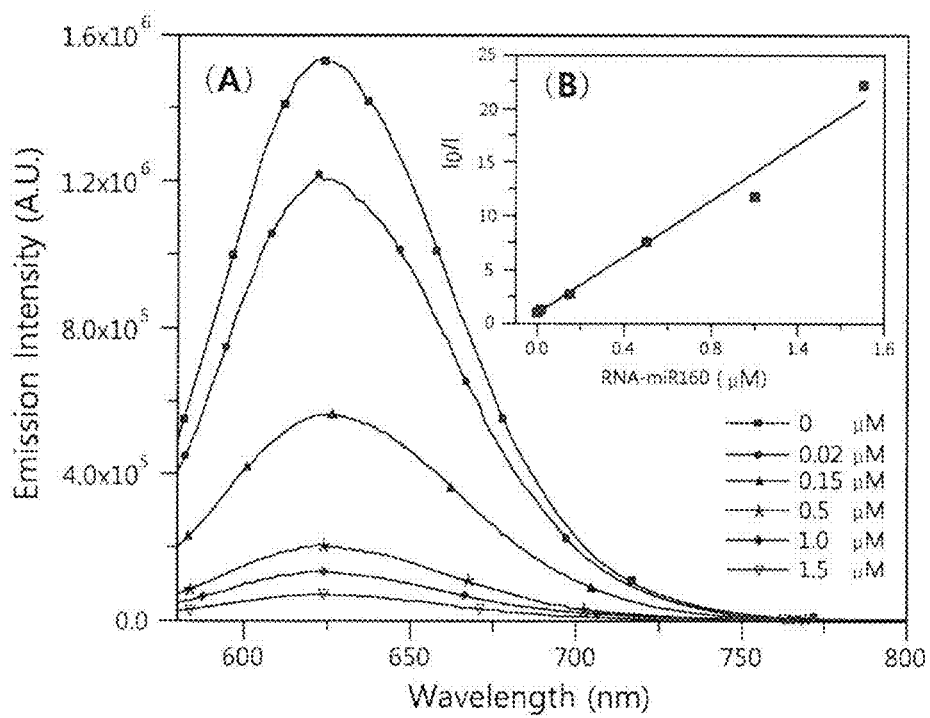
FIG. 7 shows emission spectra measured after the addition of $AgNO_3$ and reduction with $NaBH_4$ for a mixture of a silver nanocluster probe (DNA-12nt-RED-160 probe) according to an embodiment of the present invention and miR160 in the concentration from 0 µM to 1.5 µM, and a Stern-Volmer plot of the data presented in the emission spectra.

Quantifying the decrease in red emission signal, caused by the presence of the target polynucleotide as described above can be achieved by Stern-Volmer plotting as shown in FIG. 7(B). For example, as shown in FIG. 7(B), $I_0/I$ ($I_0$ is the emission intensity of a control without addition of the target polynucleotide miR160, and I is the emission intensity as a function of the concentration of miR160) shows a linear dependence versus the miR160 concentration and has a slope of about 13. If this linear dependence of the $I_0/I$ value versus the concentration of the target polynucleotide is used, the concentration of the target polynucleotide can be calculated according to a relative decrease in the emission intensity. Particularly, the silver nanocluster probe of the present invention can detect the target polypeptide miR160 for which the value of $K_d^{-1}$ is 76 nM (i.e. can detect 38 picomole of the target polypeptide miR160 in 500 μL) when the emission intensity of the silver nanocluster probe decreases by 50%, thus indicating that it can detect the target polynucleotide in the picomolar concentration. It is confirmed that the silver nanocluster probe of the present invention has very high sensitivity for detection of a target polynucleotide.

The silver nanocluster probe of the present invention and the target polynucleotide miR160 were first mixed and reacted with each other, and then treated with AgNO₃ and NaBH₄. At 1 hour after the treatment, the emission intensity was measured, and as a result, it was shown that the red emission intensity of the silver nanocluster probe clearly decreased.

Figure 8:
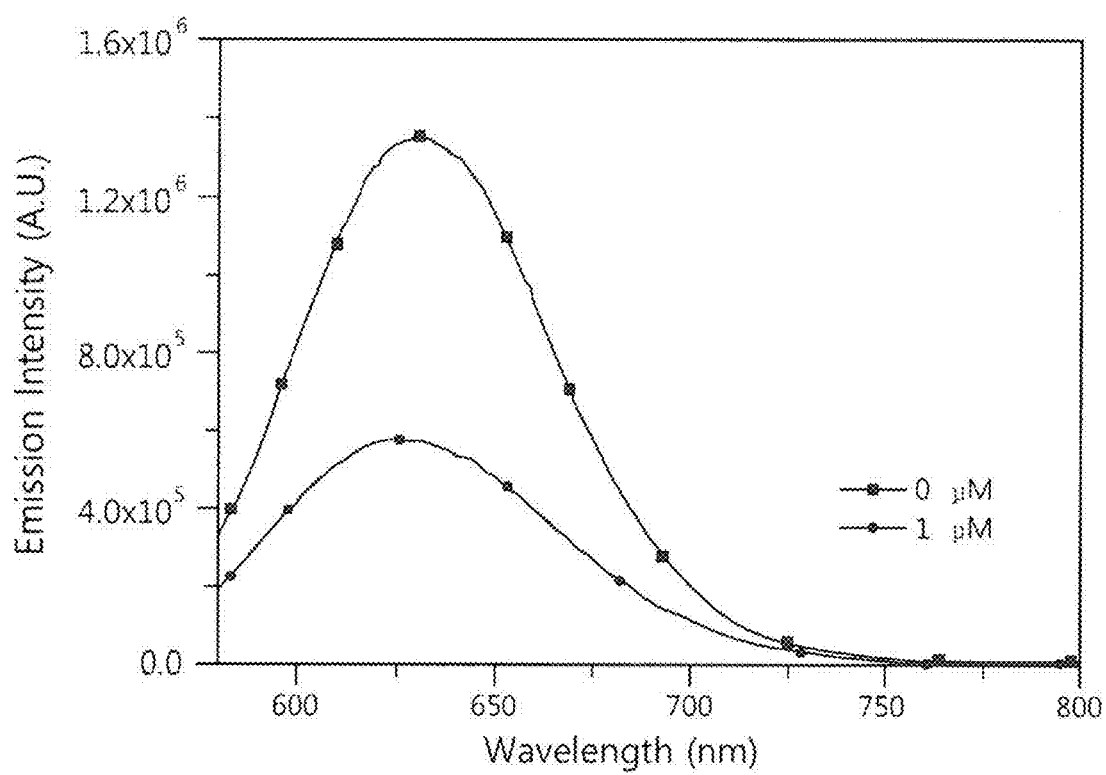
FIG. 8 shows an emission spectrum of 1.5 µM DNA-12nt-RED-160 probe, measured and recorded at 1 hour after the addition of $AgNO_3$ and $NaBH_4$ (upper curve), and a new emission spectrum measured and recorded at 20 minutes after adding the target polynucleotide miR160 to the above DNA-12nt-RED-160 probe solution (lower curve).

On the other hand. AgNO₃ and NaBH₄ were first added to the silver nanocluster probe, and then the target polynucleotide miR160 was added thereto. The emission intensity was measured. It was seen that the emission intensity of the silver nanocluster probe slightly decreased as compared with the above (see FIG. 8).

Example 3: Verification of the Specificity of the Silver Nanocluster Probe of the Present Invention Solutions were prepared by adding various concentrations (0.2 μM to 15 μM) of miR160 (target polynucleotide; SEQ ID NO: 12) to 1.5 μM of the silver nanocluster probe (DNA-12nt-RED-160 probe; SEQ ID NO: 7) prepared in Example 1 of the present invention. In addition, as a control for testing the specificity of the silver nanocluster probe (DNA-12nt-RED-160 probe) of Example 1 for miR160, solutions were prepared by adding 0.5 μM of RNA-miR163 (SEQ ID NO: 13), 0.5 μM of RNA-miR166 (SEQ ID NO: 14), 0.5 μM of RNA-miR172 (SEQ ID NO: 15) or 0.5 μM of RNA-RY-1 (SEQ ID NO: 16) to 1.5 μM of the silver nanocluster probe (DNA-12nt-RED-160 probe).

Figure 9:
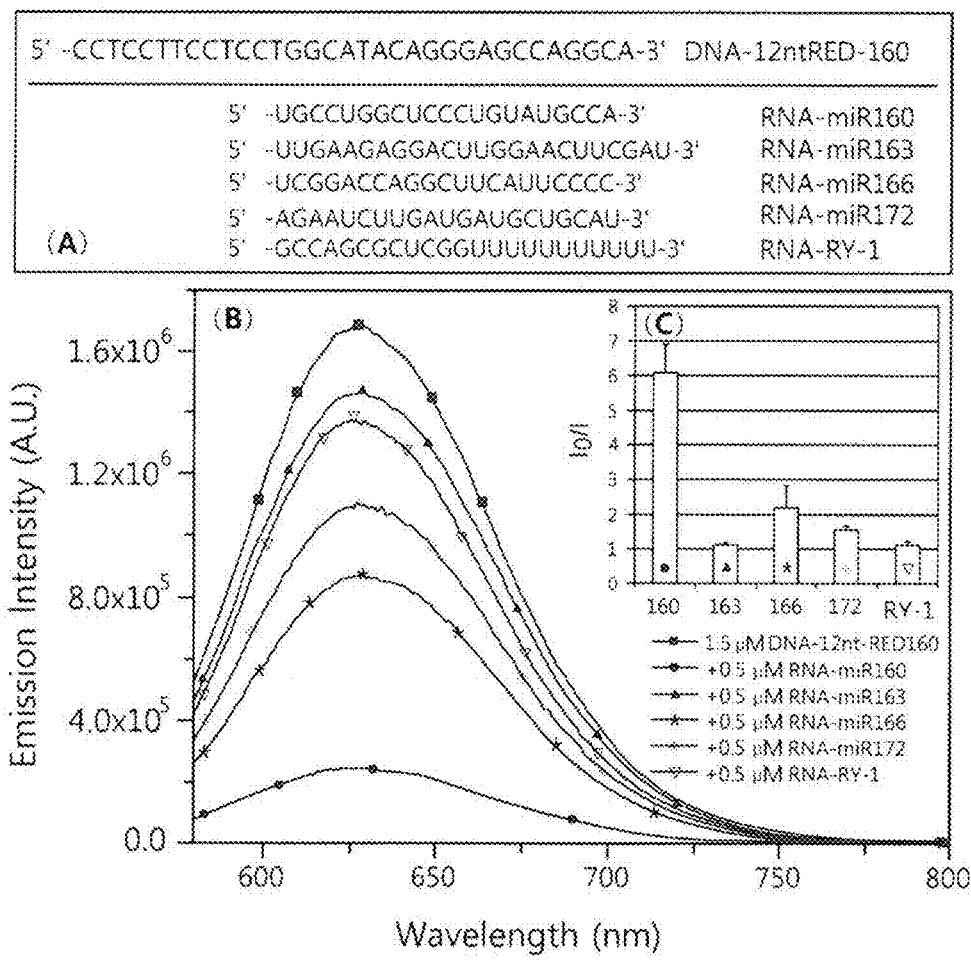
FIG. 9 shows the nucleotide sequences of the target polynucleotide miR160 and control RNAs (RNA-miR163, RNA-miR166, RNA-miR172, and RNA-RY-1), and their emission spectra and graph showing $I_0/I$ values indicating that the emission intensity of a silver nanocluster probe (DNA-12nt-RED-160 probe) according to an embodiment of the present invention decreases rapidly due to the presence of the target polynucleotide miR160.

The target polynucleotide miR160 and the control RNAs used to test the specificity of the silver nanocluster probe of the present invention have the following sequences (see FIG. 9(A)):

```
RNA-miR160:
                                    (SEQ ID NO: 12)
5'-UGCCUGGCUCCCUGUAUGCCA-3';

RNA-miR163:
                                    (SEQ ID NO: 13)
5'-UUGAAGAGGACUUGGAACUUCGAU-3';

RNA-miR166:
                                    (SEQ ID NO: 14)
5'-UCGGACCAGGCUUCAUUCCCC-3';

RNA-miR172:
                                    (SEQ ID NO: 15)
5'-AGAAUCUUGAUGAUGCUGCAU-3';

RNA-RY-1:
                                    (SEQ ID NO: 16)
5'-GCCAGCGCUCGGUUUUUUUUUUU-3'.
```

Each of the mixture solutions prepared as described above was incubated at 25° C. for 15 minutes, and AgNO₃ and NaBH₄ were added thereto to a final volume of 50 μL. In the same manner as described in Example 1, after the addition of AgNO₃ and NaBH₄ to each of the mixture solutions, each mixture solution was incubated 25° C. for 1 hour, and then 450 μL of distilled water was added thereto. The emission spectra were measured at 620 nm (after excitation at 560 nm) by a fluorimeter (Horiba Jobin Yvon, Fluoromax-4) in a 1 mm quartz cuvette (see FIG. 9(B)). Due to the presence of miR160 and the control RNAs (RNA-miR163, RNA-miR166. RNA-miR172, and RNA-RY-1), the decrease in the emission intensity of the silver nanocluster probe (DNA-12nt-RED-160 probe) was observed after the formation of silver nanoclusters. Particularly, the decrease in emission intensity caused by the target polynucleotide miR160 was very significant, but the decrease in emission intensity caused by the control RNAs was insignificant. The $I_0/I$ values for the RNAs were graphically compared with each other (FIG. 9(C)). As a result, miR160 showed the greatest decrease (6-fold decrease) in the emission intensity, confirming that the silver nanocluster probe of the present invention can detect a target polynucleotide with high specificity, and can be applied as a biosensor comprising the same.

Example 4: Detection of Wild-Type or Mutant RNA in Whole Plant RNA by the Silver Nanocluster Probe of the Present Invention In this Example, the detection of whole plant RNA subject to be analyzed was performed using the silver nanocluster probe of the present invention, and a mutant having a defect in the miRNA processing pathway was analyzed and confirmed. For this detection, the inventors used a wild-type (WT) *Arabidopsis thaliana* plant in which all RNAs, including the target polynucleotide miR160, are present, and a mutant (hyl1-2) *Arabidopsis thaliana* plant which has a defect in the miRNA processing pathway. As a result, it was shown that the silver nanocluster probe of the present invention could detect not only whether the target polynucleotide would be present in a sample including the whole plant RNA, but also whether a mutation would be present in the target polynucleotide, if present, that is, whether the target polynucleotide would be a wild-type or a mutant.

Figure 10:
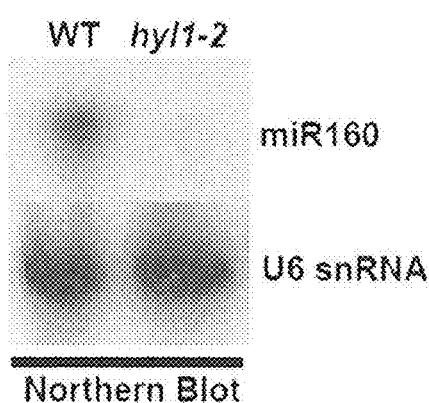
FIG. 10 is an electrophoresis image showing the results of Northern blotting for U6 snRNA and miR160 in each of wild-type (WT) and mutant (hyl1-2) *Arabidopsis thaliana* plants.

First, the purification for RNA of wild-type (WT) *Arabidopsis thaliana* and mutant (hyl1-2) *Arabidopsis thaliana* plants and Northern blot analysis were performed according to the technology known in the art (Yang, S. W.; Chen, H. Y.; Yang, J.; Machida. S.; Chua. N. H.; Yuan, Y. A. Structure 2010, 18, 594-605). As shown in FIG. 10, the band of U6 snRNA (U16 small nuclear RNA), which is not related to the miR160 processing pathway, was clearly observed both in the wild-type and mutant plants, but the level of miR160 in the mutant (hyl1-2) plant was remarkably reduced to show a smear band, as compared with that in the wild-type plant.

Next, the following experiment was performed in order to confirm whether such Northern blot analysis results are consistent with the results of analysis carried out using the silver nanocluster probe of the present invention. 20 μg of RNA obtained by redissolving the purified whole plant RNA in RNase-free distilled water instead of a 50% formamide solution, was incubated with 15 μM of the silver nanocluster probe (DNA-12nt-RED-160 probe) of the present invention at 25° C. for 15 minutes, and the silver nanocluster formation procedure (addition of $AgNO_3$ and $NaBH_4$) was performed in the same manner as described in Examples 1 to 3. According to the emission measurement method as described in Examples 1 to 3, the emission intensity for 20 μg of the whole RNA of each of wild-type (WT) *Arabidopsis thaliana* and mutant (hyl1-2) *Arabidopsis thaliana* plants was measured, and the $I_0/I$ values were calculated (see FIG. 11). For comparison, the emission intensity for 20 μg of the whole RNA of each of wild-type (WT) *Arabidopsis thaliana* and mutant (hyl1-2) *Arabidopsis thaliana* plants caused by the formation of silver nanoparticle clusters without adding the silver nanocluster probe (DNA-12nt-RED-160 probe) was measured (see FIG. 12).

Figure 11:
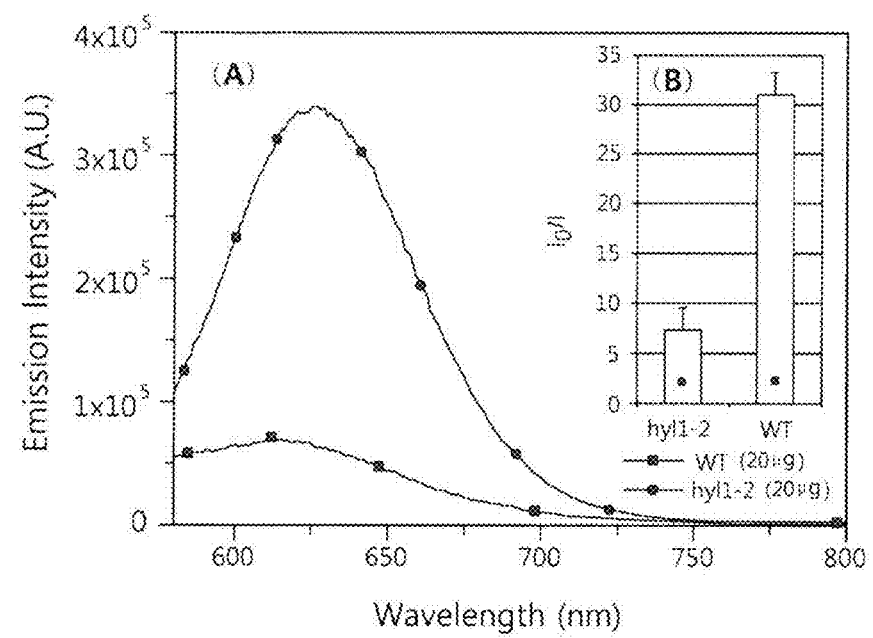
FIG. 11 shows emission spectra recorded by measuring light emission caused by the formation of silver nanoparticle clusters, after the reaction between the whole RNA of wild-type (WT) or mutant (hyl1-2) *Arabidopsis thaliana* plant and a silver nanocluster probe DNA-12nt-RED-160 probe) according to an embodiment of the present invention, and a graph showing $I_0/I$ values (insert).
Figure 12:
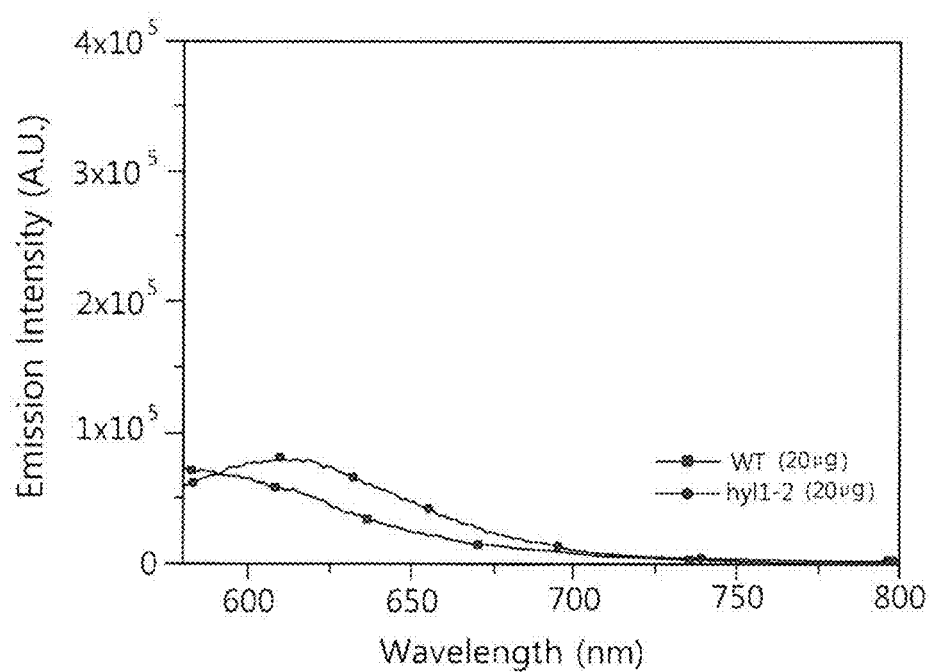
FIG. 12 shows emission spectra recorded by measuring light emission caused by the formation of silver nanoparticle clusters, without adding a silver nanocluster probe (DNA-12nt-RED-160 probe) according to an embodiment of the present invention to the whole RNA of each of wild-type (WT) and mutant (hyl1-2) *Arabidopsis thaliana* plants.

As a result, as shown in FIG. 11, in the case that the silver nanocluster probe (DNA-12nt-RED-160 probe) was reacted with the whole RNA of the wild-type *Arabidopsis thaliana* plant, a significant decrease in the emission intensity (lower curve) was observed, whereas in the case that the silver nanocluster probe (DNA-12nt-RED-160 probe) was reacted with the whole RNA of the mutant (hyl1-2) *Arabidopsis thaliana* plant, a decrease in the emission intensity was insignificant, and the emission intensity was about 4 times higher than that for the wild-type plant (upper curve). This suggests that the silver nanocluster probe (DNA-12nt-RED-160 probe) of the present invention does not bind specifically to the mutant miR160, and thus a decrease in the emission intensity is insignificant. These results are consistent with the results of Northern blot analysis performed as described above. In other words, in this Example, a mutant having a defect in the miRNA processing pathway could be detected in the whole plant RNA using the silver nanocluster probe of the present invention. Accordingly, the silver nanocluster probe of the present invention can detect not only whether the target polynucleotide is present in a sample including the whole RNA, but also whether a mutation is present in the target polynucleotide, if present, that is, whether the target polynucleotide is a wild-type or a mutant.

As a result, it was confirmed that the results of the experiment performed using the silver nanocluster probe of the present invention (FIG. 11) were consistent with the results of Northern blot analysis (FIG. 10). Thus, when determining whether a specific target polynucleotide is present in a sample including the whole RNA, the silver nanocluster probe of the present invention can produce a clear detection signal even in the presence of the non-specific background values of the whole RNA, and thus it can effectively detect the target polynucleotide. In addition, the silver nanocluster probe of the present invention makes it possible to determine whether a mutation is present in the target polynucleotide, that is, whether the target polynucleotide is a wild-type or a mutant. Accordingly, the silver nanocluster probe of the present invention can be applied as a flatform technology for a novel biosensor in various fields.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

We claim:

1. A silver nanocluster probe having the following structural formula 1 and specifically binding to a target polynucleotide:

X-5'-Y-3' or 5'-Y-3'-X         Structural Formula 1 wherein X is a silver nanoparticle binding region, wherein X is an oligonucleotide selected from the group consisting of any one of SEQ ID NOs: 1 to 5, the silver nanoparticle binding region being allowed to be bound to silver nanoparticles and to form a silver nanocluster together with the silver nanoparticles;

Y is an oligonucleotide comprising a specific nucleotide sequence region, the specific nucleotide sequence region being allowed to be specifically bound to a target polynucleotide, and the 5' or 3' end of Y being linked to X of structural formula 1, provided that when X is SEQ ID NOs: 1, 2, 4 or 5 the structural formula I is 5'-Y-3'-X; and wherein the silver nanocluster probe emits detectable light when the silver nanoparticles bind to the silver nanoparticle binding region X and form the silver nanocluster, but the light emission from the silver nanocluster probe decreases or decays when the target polynucleotide binds to the specific nucleotide sequence region Y.

2. The silver nanocluster probe of claim 1, wherein the target polynucleotide is miRNA 160, and Y is an oligonucleotide of SEQ ID NO: 6.

3. The silver nanocluster probe of claim 2, wherein the probe is an oligonucleotide of SEQ ID NO: 9.

4. The silver nanocluster probe of claim 1, wherein the emitted light has a wavelength from red to infrared wavelength range.

5. The silver nanocluster probe of claim 4, wherein the emitted light has a wavelength of between 600 nm and 750 nm.

6. A method for detecting a target polynucleotide using a silver nanocluster probe, the method comprising the steps of:

(a) preparing a silver nanocluster probe that has the following structural formula 1 and that specifically binds to a target polynucleotide:

X-5'Y-3' or 5'-Y-3'-X          Structural Formula 1

(b) allowing the target polynucleotide to bind complementarily to Y of structural formula 1, Y being an oligonucleotide comprising a specific nucleotide sequence region that is specifically bound to the target polynucleotide, and the 5' or 3' end of Y being linked to X of structural formula 1;

(c) binding silver nanoparticles to X of structural formula 1 that is a silver nanoparticle binding region, wherein X is an oligonucleotide selected from the group consisting of any one of SEQ ID NOs: 1 to 5, the silver nanoparticle binding region forming a silver nanocluster together with the silver nanoparticles; and (d) determining that the intensity of light emitted from the silver nanocluster formed by the binding of the silver nanoparticles to X of structural formula 1 decreases or decays, according to the binding of the target polynucleotide to Y of structural formula 1.

7. The method of claim 6, further comprising a step of quantifying a decrease in the intensity of the emitted light and quantifying the target polynucleotide based on $I_0/I$, wherein $I_0$ is the intensity of the light emitted from the silver nanocluster formed by the binding of the silver nanoparticles to X of structural formula 1 when the target polynucleotide is not present, and I is the intensity of the light determined to decrease or decay in step (d).

8. The method of claim 6, further comprising a step of detecting either the presence of the target polynucleotide in a sample or a mutation in the target polynucleotide by determining whether the intensity of the light decreases or decays.

9. The method of claim 6, wherein step (c) is performed by addition of $AgNO_3$ and reduction with $NaBH_4$.

10. The method of claim 6, wherein the emitted light has a wavelength from red to infrared wavelength range.

11. The method of claim 10, wherein the emitted light has a wavelength of between 600 nm and 750 nm.

12. The method of claim 6, wherein the target polynucleotide is miRNA, and Y is an oligonucleotide of complementary sequence to the target miRNA.

13. The method of claim 6, wherein the target polynucleotide is miRNA 160, and Y is an oligonucleotide of SEQ ID NO: 6.

14. The method of claim 6, wherein the probe is an oligonucleotide selected from the group consisting of SEQ ID NOs: 7 to 11.

15. A silver nanocluster probe of formula X-5'-Y-3':

wherein X is a silver nanoparticle binding region, wherein X is an oligonucleotide selected from the group consisting of any one of SEQ ID NOs: 1, 2, 4 or 5, the silver nanoparticle binding region being allowed to be bound to silver nanoparticles and to form a silver nanocluster together with the silver nanoparticles;

Y is an oligonucleotide of SEQ ID NO: 6; and wherein the silver nanocluster probe emits detectable light when the silver nanoparticles bind to the silver nanoparticle binding region X and form the silver nanocluster, but the light emission from the silver nanocluster probe decreases or decays when the target polynucleotide binds to the specific nucleotide sequence region Y.

16. The silver nanocluster probe of claim 15, wherein the probe is an oligonucleotide selected from the group consisting of SEQ ID NOs: 7, 8, 10 or 11.

17. The silver nanocluster probe of claim 15, wherein the emitted light has a wavelength from red to infrared wavelength range.

18. The silver nanocluster probe of claim 15, wherein the emitted light has a wavelength of between 600 nm and 750 nm.

19. The silver nanocluster probe of claim 1, wherein Y is an oligonucleotide of complementary sequence to a target RNA sequence.

20. The silver nanocluster probe of claim 1, wherein Y is an oligonucleotide of complementary sequence to a target miRNA sequence.

* * * * *